US008676284B2

(12) United States Patent
He

(10) Patent No.: US 8,676,284 B2
(45) Date of Patent: Mar. 18, 2014

(54) METHOD FOR NON-INVASIVE BLOOD GLUCOSE MONITORING

(75) Inventor: Zongyan He, Kendall Park, NJ (US)

(73) Assignee: Novanex, Inc., North Brunswick, NJ (US)

(*) Notice: Subject to any disclaimer, the term of this patent is extended or adjusted under 35 U.S.C. 154(b) by 622 days.

(21) Appl. No.: 12/905,817

(22) Filed: Oct. 15, 2010

(65) Prior Publication Data

US 2012/0095303 A1  Apr. 19, 2012

(51) Int. Cl.
*A61B 5/1455* (2006.01)
(52) U.S. Cl.
USPC .............................. 600/316; 600/310; 600/322
(58) Field of Classification Search
USPC .................................. 600/300–529
See application file for complete search history.

(56) References Cited

U.S. PATENT DOCUMENTS

| 5,795,305 | A | 8/1998 | Cho et al. |
|---|---|---|---|
| 5,924,996 | A | 7/1999 | Cho et al. |
| 7,251,514 | B2 | 7/2007 | Cho et al. |
| 7,254,428 | B2 | 8/2007 | Cho et al. |
| 2003/0109998 | A1 | 6/2003 | Lorenz et al. |
| 2005/0043630 | A1* | 2/2005 | Buchert ........................ 600/473 |
| 2005/0192492 | A1 | 9/2005 | Cho et al. |
| 2008/0200781 | A1 | 8/2008 | Van Herpen et al. |

FOREIGN PATENT DOCUMENTS

| JP | 2003-129020 | 5/2003 |
|---|---|---|
| JP | 2003-178619 | 6/2003 |
| JP | 2003-195455 | 7/2003 |
| JP | 2003-331857 | 9/2003 |
| JP | 2003-338580 | 9/2003 |
| JP | 2003-349792 | 10/2003 |
| JP | 2003-404677 | 12/2003 |
| WO | 2008141306 A2 | 11/2008 |

OTHER PUBLICATIONS

International Search Report mailed May 25, 2012 for PCT Application No. PCT/US2011/054885.
PCT Written Opinion of International Search Authority mailed May 25, 2012 for PCT Application No. PCT/US201/054885.

* cited by examiner

*Primary Examiner* — Eric Winakur
*Assistant Examiner* — Marjan Fardanesh
(74) *Attorney, Agent, or Firm* — Moser Taboada

(57) ABSTRACT

A method for noninvasive blood glucose monitoring involves metabolic heat measurement and algorithm to correct interferences from environmental factors, and physiological or pathological conditions of subjects.

21 Claims, 1 Drawing Sheet

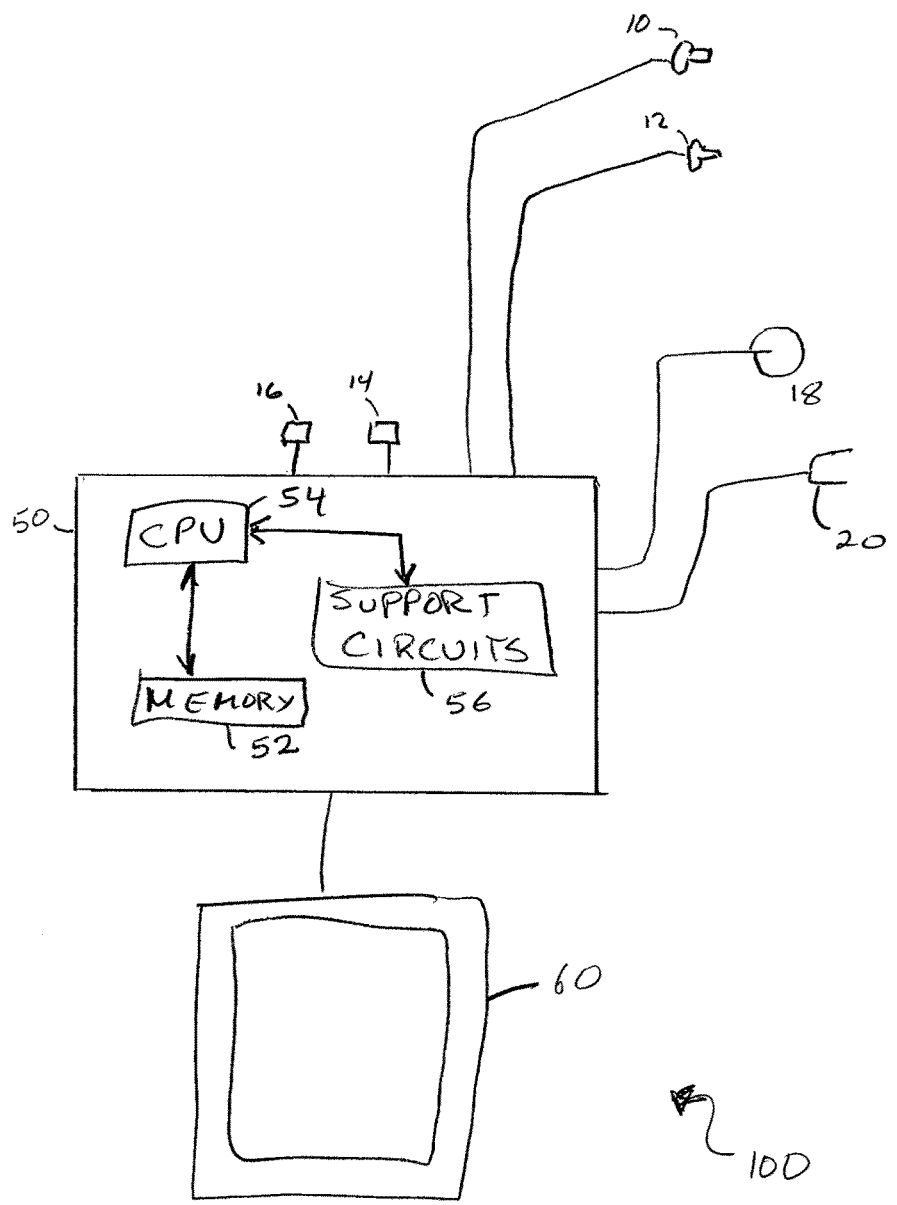

METHOD FOR NON-INVASIVE BLOOD GLUCOSE MONITORING

This invention relates to a method for noninvasive blood glucose monitoring. More specifically, this invention relates to methods for metabolic heat measurement and its use on noninvasive blood glucose monitoring, and further methods for removing interferences from environmental factors and subject's physiological or pathological conditions.

Diabettes (diabetes mellitus) is a group of metabolic syndrome caused by interactions of genetic and environmental factors. Because defects of insulin secretion, insulin action or both, carbohydrates, protein, fat, water and electrolyte metabolism disorders are occurred. Its main common characteristic in clinic is chronic (long term) hyperglycemia. World-wide there are about 132 million diabetics, and the number is projected to reach 240 million by 2010, among them about ¾ new diabetes are in developing countries. The increase rate is nearly at 10 million per year.

The mechanism of diabetic etiology and pathogenesis has not been fully understood yet, therefore the treatment is not effective. Treatment goals are to eliminate symptoms, to maintain a normal quality of life and work capability, to prevent the occurrence of acute metabolic disorder, and to prevent and delay the occurrence and development of chronic complications. Therefore, diabetes treatment is lifelong process. In addition to insulin and hypoglycemic drugs, diet is the basis for the treatment of diabetes. In all treatments, blood glucose monitoring is crucial.

Most of methods for blood glucose measurement are invasive. Sample blood from patients is taken and the glucose level is measured, typically by glucose oxidase (GOx) method. Venous whole blood, plasma or serum glucose is tested in hospitals. Capillary whole blood glucose can be checked on a portable device operated by a patient. To maintain the glucose at a desired level, the blood glucose has to be tested several times per day, including at least before and after the three meals and before bed. If a patient suffers nocturnal hypoglycemia, additional testing is needed. All of these methods accurately obtain a blood glucose level, but there are problems and limitations. First, it is very painful to take blood samples multiple times per day. Second, it is costly to use glucose oxidase reagents or test strips either in hospital or at home, which presents a significant financial burden to patients. In addition, self-testing at home may lead to blood contamination and bacterial infection.

Therefore development of a non-invasive type of blood glucose monitoring technologies and devices has been a long-term goal of many research institutions and companies.

Non-invasive simple urine tests have gradually been phased out, because a urine-positive result only provides an important clue, but does not provide a sufficient basis for diagnosis. Even if urine test is negative, diabetes cannot be ruled out. Testing saliva provides an alternative. One proposal introduces an optical method for detection of glucose in saliva. As the glucose level in saliva is low, only ⅕₀ to ¹⁄₁₀₀ to that in blood, the sensitivity and accuracy needed for this measurement difficult to achieve. Sweat has also become another target for glucose detection. Another proposal collects sweat and tissue fluid on the surface of finger, and uses a glucose oxidase assay to obtain the glucose levels. Another proposal uses a subcutaneous fluid extractor. The secretions from stratum corneum are collected through the skin and then tested with an enzymatic test. The disadvantages of these methods include that it is hard to achieve accuracy, complicated device structures are needed, and they are dependent on the costly glucose oxidase reagents.

Apart from the methods using samples of urine, saliva, sweat and skin tissue fluid, other methods make use of various physical and chemical effects to measure blood glucose from the skin. One method provides a counter-ion penetration device. The device applies a very small current through the intact skin then a glucose sample is collected on a gel plate that has embedded glucose oxidase. When the glucose sample is applied to the plate, it is converted to hydrogen peroxide and detected by a biosensor. Another proposal is for a so-called pulse impedance non-invasive device and method for detection of blood glucose or other blood components. The detection equipment consists of a main control unit, a sweep current source, a measurement unit, an alarm unit, a storage unit and a communication interface. A pair of excitation electrodes is connected to the current source, and another pair of measurement electrodes to the measurement unit. The main control unit controls the entire measurement system to process dynamic impedance pulse wave data, and then to calculate blood glucose and other components in blood. This method is based on the assumption that a dynamic pulse wave impedance spectrum and the blood glucose level are correlated, but this relationship lacks rigorous experimental evidence. Another proposal applies a magnetic field to the sample (e.g. blood),then an analyte (e.g. glucose) concentration is determined from the Rf signal amplitude at a characteristic frequency.

The use of optical methods for direct measurement of skin capillary whole blood glucose has been reported. These methods generally apply a variety of different types of light radiation (such as the far-infrared) on a part of the body (such as skin and ears). The blood glucose level is related to the light reflection or the transmission, with photoelectric conversion and numerical analysis techniques used to convert the light signal to blood glucose concentration. These methods need to address 1) error from individual patient differences, and differences in test positions and skin conditions, 2) accuracy and reliability of the measurement, and 3) interference from other components in blood.

Another proposal provides a non-acupuncture device and a method to measure blood glucose concentration. In the operation, the device is self-standardized, and does not reply on reference samples. The device uses the principle that the attenuation of total reflection infrared spectroscopy is related to blood glucose concentration. By applying an infrared light to human tissue (e.g. finger), and comparing the characteristics of the infrared spectrum in two regions, this device seeks to calculate the blood glucose level. This approach also has many of the difficulties of the above-mentioned methods, such as differences in skin stratum corneum (thickness, transparency, dryness, amount of fat, etc.) that causes test data distortion.

U.S. Patent (U.S. Pat. Nos. 5,795,305 and 5,924,996) and a series of patent documents by Hitachi Ltd., (JP 2003-195455, JP 2003-178619, JP 2003-129020, JP 2003-338580, JP 2003-331857, JP 2003-349792, JP 2003-404677, U.S. Pat. Nos. 7,254,428, 7,251,514, US 2005-0192492) present a methods for measuring blood glucose through skin temperature. The methods and devices operate without blood sampling, and enhance the measurement results using data on oxygen saturation and blood flow volume. Three units are typically included in this equipment: (1) a temperature measurement unit to measure the number points of surface temperature, to get information used to compute the surface heat dissipation from the convective heat transfer and radiation heat transfer, (2) blood flow volume measurement unit to obtain the status of blood flow at the measurement points, and (3) oxygen saturation measurement unit to obtain blood oxygen content at measurement points. The method described does not consider other factors that affect the accuracy of the surface temperature measurement, such as external temperature, humidity, air flow, clothing, sensor and skin contact condition, thickness of skin, and color of skin, and the influence of current body physiological and pathological conditions, such as movement, differences in basal metabolic rate, fever, hyperthyroidism, liver disease, and the like. It is not enough to just use the blood flow volume and oxygen concentration to compliment the surface heat dissipation data. In addition, the methods do not sufficiently address the complex relationship between various parameters, the cumulative effect of various detection errors, and the elimination of other interference factors.

Non-invasive glucose monitors are barely found in market. In the United States and Japan, several products have been developed using sweat and skin tissue fluid samples. However, the available devices are generally conventional invasive blood glucose meters available everywhere. Although there are numerous patents on non-invasive detection, there is still a long way to realize a real product to meet the actual needs of patients.

SUMMARY OF THE INVENTION

Various aspects of this invention provide a direct and effective method to realize a new, reliable and relatively simple non-invasive blood glucose monitoring. This method is based on the principle that blood glucose level and body tissue metabolic rate is proportionally related. Experimental results show that probe temperature changes over short periods (e.g. from a probe placed on a particular part of the body) is strongly related to the current blood glucose concentration. If the shape, size, material, heat capacity and other parameters of the probe are kept constant, and the environmental temperature and the initial temperature of the probe are below the body temperature in a certain range, the blood glucose concentration is significantly correlated to the parameters of the probe temperature rise rate over in a certain time period. Therefore, blood glucose concentrations can be detected through measuring those parameters.

In one aspect, this invention controls additional factors that interfere with the accuracy of the above measurements based on body heat dissipation, such as: environmental temperature and humidity, and the current physical condition of device user. In various embodiments of this invention are methods to eliminate these interferences and to obtain a more accurate measurement of blood glucose.

In one embodiment, provided is a method for noninvasively determining blood glucose in a subject, comprising: (a) in body cavity(s) measuring: a blood glucose index that is a period for a defined temperature rise or temperature rise for a defined period; and a local humidity; (b) measuring an environmental temperature; (c) measuring an environmental humidity; and (d) deducing from the measured values and calibration data including chemically measured blood glucose the current blood glucose value. In another embodiment, the method further comprises measuring a basal body temperature, and using it in the deducing. In another embodiment, the method further comprises measuring a basal metabolism, and using it in the deducing. In another embodiment, the method further comprises measuring a body temperature (i.e., local temperature), and using it in the deducing. In yet another embodiment, the a blood glucose index is measured in an ear canal. In still another embodiment, the local humidity and body temperature are measured in an ear canal, and the local body temperature is used in the deducing.

In another embodiment, the method further comprises measuring one or more of a pulse or a blood oxygen level, and using one or both in the deducing.

In a further embodiment, the method further comprises: (e) inputting data including one or more of fasting blood glucose, 2-hour postprandial blood glucose, basal body temperature, basal metabolic rate or medical condition data; (f) categorizing the subject into one of at least two categories; (g) selecting one of two or more separate empirical formulas dependent on the categorizing; and (d') conducting the deducing with the selected empirical formula.

In a still further embodiment, the categorization is in part based on whether a normal range of fasting blood glucose or one or more ranges of elevated fasting blood glucose pertains. In a still further embodiment, the categorization is in part based on whether a low range, normal range, or elevated range of 2-hour postprandial blood glucose pertains. In a still further embodiment, the categorization is in part based on whether a low range, a normal range, or one or more elevated ranges of basal body temperature pertains. In a still further embodiment, the categorization is in part based on whether one or more low ranges, a normal range, or one or more elevated ranges of basal metabolism pertains. In a still further embodiment, calibration data including chemically measured blood glucose includes data taken under the basal metabolic state. In a still further embodiment, calibration data including chemically measured blood glucose further includes data taken the subjects more current physiological state. In a still further embodiment, the blood glucose index is measured in one ear canal, and the local humidity is measured in the second ear canal. In a still further embodiment, the blood glucose index is measured in one ear canal, and the local humidity and body temperature are measured in the second ear canal.

In another embodiment, deducing utilizes a estimate for the normal body temperature at the given time of day of the operation of the method, and wherein the estimate for various times of day are refined from data collected with each operation of the method.

In still another embodiment, provided is an apparatus for measuring the blood glucose index comprising: (a) a controller; (b) connected to the controller, a blood glucose index probe; (c) connected to the controller, local humidity probe; (d) connected to the controller, an environmental temperature probe; and (e) connected to the controller, an environmental humidity probe, wherein the controller is programmed to deduce from values obtained from the probes and calibration data including chemically measured blood glucose the current blood glucose value, and wherein the controller can be connected to a probe body temperature and/or a probe for heart rate and/or a probe for blood oxygen saturation, and can use the values obtained from one or more of these probes to deduce the current blood glucose value.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only illustrative embodiments of this invention and are therefore not to be considered limiting of its scope, for the invention may admit to other equally effective embodiments.

The FIGURE shows an illustrative device for measuring the blood glucose index.

To facilitate understanding, identical reference numerals have been used, where possible, to designate comparable elements that are common to the figures. The figures are not drawn to scale and may be simplified for clarity. It is contemplated that elements and features of one embodiment may be beneficially incorporated in other embodiments without further recitation.

DETAILED DESCRIPTION

The following provides a description of this non-invasive blood glucose monitoring method.

1. Basic Principles

Studies have shown that sugar in food provides more than 70% energy that the body needs. Glucose is a digestion and metabolic conversion product of carbohydrates and is stored in form of glycogen in liver and muscle. However, many cells in the body tissues do not store glycogen. They rely on glucose uptake from the blood to meet the needs of their metabolic and functional activities. Blood glucose, primarily by way of facilitated diffusion, enters into these cells. Therefore, to maintain the blood glucose concentration at a certain level is important. If the concentration is too low, glucose does not effectively diffuse into the cells; while the concentration is too high, a lot of glucose is lost through the kidneys into urine. Under regulation of a nervous—body fluids feedback mechanism, the blood sugar level maintains homeostasis; the glucose consumption can be replenished from the glycogen in liver; and when blood glucose concentration increases, such as postprandial increases of sugar from food, glucose is converted into glycogen and stored in liver. In this homeostasis, insulin and other hormones play an important role. An increase of blood glucose level rapidly induces insulin secretion, which will enable the organs to accelerate their uptake, consumption and storage of glucose, and then result in decrease of blood glucose level.

Therefore, when the blood glucose level increases, the body heat production or the metabolic rate will be increased by at least two factors. The first is mainly the role of the physical factors. The increased concentration of glucose accelerates the diffusion process, which causes cells to more easily access to glucose, and then accelerate metabolic processes utilizing glucose, which will inevitably generate extra heat. The second is mainly the role of biochemical factors. The rapid secretion of insulin promotes the organs to uptake and use glucose, which results in extra heat production.

Sophisticated experiments have shown that the effect of the extra heat is not evenly distributed in the body. In some parts, such as in brain and ears that are close to the head cavity, the extra heat effect is more obvious than that in other parts. The rate of the extra heat production is up to 80% within minutes after eating, which is related to the brain energy consumption that is much higher than other organs, and is derived from the metabolic oxidation of glucose. In these parts, the extra heat production results from the two factors mentioned above, and is not the general food specific dynamic effect. (The so-called specific dynamic effect is a phenomenon that after eating heat production is additionally higher than that before. However, this kind of effect usually happens around 1 hour after eating, and extends in 7-8 hours. The heat production is also related to food categories. For mixed foods, only an additional 10% calories is produced.) In other words, even if insulin secretion decreases or insulin resistance exists, due to the role of the first factor, the body is able to generate significant extra heat. Conversely, due to brain metabolism being reliant on glucose in the blood, when glucose concentration is too low, facilitated diffusion will be reduced. Thus, the brain metabolic rate will be decreased, and then heat production will be reduced. If the liver glycogen under the action of glucagon cannot be transferred to glucose into the blood-stream, coma or even seizures arise.

In summary, the levels of blood glucose are positively correlated to the body heat production through the two mechanisms. If the effect of the body heat production at any given time can be accurately measured and standardized, the blood glucose level at that time can be obtained. If this heat measurement is noninvasive and fast, the non-invasive detection and monitoring of blood glucose can be achieved.

2. Detailed Method

It should be noted that the body heat produced at a moment does not mean the body temperature increase or decrease at that moment, because the heat produced by the body mainly emits from the body surface to outside environment, and small portions are taken away by the exhalation, excretion, and secretion. Under normal physiological conditions, the rate of heat production and dissipation are almost balanced, such that more heat production yields more heat dissipation, and vice versa. Therefore, the body temperature always maintain relatively constant. Of course, there is cyclical fluctuation of the body temperature in a day and night, the lowest at 4-5 AM and the highest at 4-5 PM. However, the daily body temperature rhythm (circadian rhythm) is an inner rhythm that is only consistent with the Earth rotation period, and not with muscle activity, oxygen consumption and eating. It is difficult to quantify the effect of body heat simply by the detection of deep body temperature; therefore, the metabolic heat emitted from the body can be obtained through a skin temperature measurement.

The human surface temperature (skin temperature) is interfered seriously by various factors of the environment and the subjects themselves, because the skin temperature and the local blood flow are closely related. The skin temperature varies with all the factors that affect the skin vasodilation and contraction, which factors interfere the measurement of blood glucose from metabolic heat. For example, in cold environments, due to skin vasoconstriction and bloodflow reduction, the skin temperature falls and reduces body heat dissipation. On the other hand, in warm environment, due to skin vessel dilation and the blood flow increase, the skin temperature rises in excess of body heat dissipation. Emotional state is another factor. The skin temperature, especially on the hand, is decreased significantly, when a person is in a highly emotional state, the vascular tension is increased, and then the blood flow is reduced. Experiments show that when one is in high emotion, the finger skin temperature is decreased from 30° C. to 24° C., and gradually recovers after the emotion is relieved. Another example is with fever, where skin temperature shows an obvious increase.

There are two approaches to overcome such interferences. The first approach is to detect the skin temperature, along with the simultaneous detection of local blood flow. Through the calibration with the blood glucose level under normal blood flow, an empirical formula can be used to modify the blood glucose level from the measurement of the skin temperature. The above mentioned US and Japanese patents adopted this approach. The second approach is to measure an initial temperature, along with environmental temperature and humidity. By the comparison of the parameters and honing the empirical relationship via calibration measurements, the blood glucose level is calculated.

The first approach seems easier, but in reality this may not be the case. The aforementioned U.S. patents are related to the detection at the fingertip. The skin temperature at the fingertip is affected by many factors (temperature, humidity, wind speed, muscle movement, skin condition, sweat, and emotion, etc.). Accurate detection of the blood flow is also difficult. Even if the blood flow is detected, the actual blood glucose is still difficult to obtain from the calibration with these parameters. This is because the blood flow and blood oxygen concentration cannot fully reflect the physiological or pathological state that affects the blood glucose level obtained from temperature measurement. Examples are given below:

1) When in fever, the blood flow and the oxygen saturation may not be changed much, but the skin temperature is increased significantly, and therefore the blood glucose level obtained by measuring skin temperature is much higher than its actual level.

2) The basal metabolic rate and basal body temperature of patients with physiological or pathological disorders (e.g., hyperthyroidism, polycythemia, leukemia, etc.) are higher than those of the normal subjects. Due to excessive secretion of T3 and T4 and the increase of sympathetic activity, rapid metabolism significantly increases heat production and heat dissipation, and heat production from the glucose oxidation after meal is high. These heats are superimposed to the basal metabolic heat, which may not be a completely linear superposition. Postprandial heat production is often lower than the actual blood glucose value might imply. This is because the human body temperature cannot be arbitrarily increased. To maintain the temperature in the normal range, the excess heat is dissipated in forms of radiation, conduction, convection, skin moisture evaporation, respiratory evaporation, breath, urine and fecal excretion, and the like. (The heat dissipation in the last several forms takes a very small proportion of the body heat dissipation.) Tested subjects with high metabolic disorder often feel hungry; have high appetite, are not intolerant of warmth, sweat a lot, and their skin is warm and moist. Therefore, of the various forms of the heat dissipation, their skin evaporation is much higher than the average person's. This evaporation can be classified into senseless evaporation and sweating, and both are influenced by environmental humidity. Such heat transfer by phase change is very difficult to accurately detect, and is not detectable only by measuring at the fingertip (see the aforementioned U.S. and Japanese patents). According to the inventor's experiment, because the skin evaporative heat is difficult to be measured, the metabolic heat obtained by using a temperature probe from the subject after a meal is usually low, so that the inferred blood glucose level after meal is often low (relative to GOx measurement).

3) The basal body temperature of women in reproductive age is about 0.3-0.5° C. higher after ovulation those that before ovulation, and the metabolic heat is changed accordingly. But the blood flow and the oxygen concentration are not changed during this period. To measure blood glucose accurately, blood glucose should be calibrated before and after the period. But one needs to determine the menstruation cycle of the subject. So the first method is not practical to eliminate the interferences from physiological or pathological interferences.

On another hand, in the second approach, although the workload is large for accurate measurements of for example the environmental temperature and humidity, the measurement site humidity, the basal body temperature, the basal metabolic rate, the body temperature, the pulse, and the other physiological parameters, can be measured and an empirical formula for glucose detection can be established, through which the major environmental, physiological or pathological interference factors can be corrected. This is an important idea of the present invention.

3. Detection Position:

An embodiment of the method in the present invention is the selection of detection position where the disturbances from the environment and the body itself are small and the amount of metabolic heat production is large. A useful embodiment of the detection position is the ear canal, or another enclosed cavity.

(1) Skin temperature on the surfaces of the human body varies. At 23° C. room temperature, the skin temperature on the foot is 27° C., the hand 30° C., the forehead 33-34° C. When the environment temperature exceeds 32° C., the differences of the skin temperature are reduced. In cold environment, when the temperature drops, the skin temperature on hand and foot decrease most significantly. On all exposed parts, the skin temperature on head has the smallest variation. The ear canal is in the head, where the temperature interference from environment temperature is small.

(2) Brain weight accounts for only about 2% of body weight. However, in a quiet state, the brain circulatory system takes about 13% of the circulating blood, which indicates that there is a very high level of metabolism in brain tissue. The oxygen consumption of the brain is 20 times that of the muscle tissue. However, it has been reported that in sleep and active state, there is little difference in the brain's glucose metabolism. When a person focuses on thinking, the increase of the heat production is typically not more than 4%. Thus, metabolic heat production effect in the ear canal, which is near the brain, is greater than that in other parts of the body, and is less affected by the states of the brain activities.

(3) Reports from a large number of experiments indicate that the tympanic temperature is roughly proportional to hypothalamic temperature, so that in physiological experiments the tympanic membrane temperature is commonly used as a proxy for temperature in the brain.

(4) The detection probe can be designed in the shape of human ears, such that the probe can be placed into the ear canal to form a partially closed chamber within the ear. The interferences of environmental factors such as temperature, air flow (breeze), external humidity, and the like can thus be minimized.

In summary, the metabolic heat emanating from the ear canal is very significant and relatively stable, i.e., it is not significantly affected by the brain activity and the environmental factors. As the probe placed into the ears does not directly touch the skin, the temperature measurement is a temperature effect for a certain period of time (or the time of a temperature effect). Based on these principles, the embodiment method of this invention is actually a temperature measurement between the deep body temperature and the skin temperature.

4. Personalized Detection Mode

As mentioned earlier, apart from environmental factors, the interference of physiological or pathological factors should also be excluded. Therefore, in an embodiment of the present invention, the basic physiological or pathological states of the subjects will be first determined and classified according to the recent blood glucose level, the basal body temperature and the metabolic rate, and the other physiological or pathological conditions of the subject. The instrument can be programmed to automatically select the blood sugar correction method and formula to adjust the detection data to an actual blood glucose level according to the specific conditions of users. The embodiment of this invention takes the following steps to determine subject's physiological or pathological conditions:

(1) By measuring the basal body temperature and the basal metabolic rate, the instrument gets information of the subject's physiological and/or pathological conditions related the metabolism.

(2) The instrument gets further information of the subject's physiological and pathological conditions, such as through a series of questionnaires on the instrument interface, such as age, gender, weight, height, recent fasting blood glucose levels, two recent 2-hour postprandial blood glucose levels (e.g. a GOx determination), whether long-term fever, hyperthyroidism, liver dysfunction, hypercortisolism, acromegaly, pancreatic disease, glucagon tumor, polycythemia, leukemia and heart disease associated with breathing difficulties; kidney disease, Addison's disease, adrenal cortex and pituitary function, and pathologic reduction of hunger and other diseases; chronic bronchitis, emphysema and bronchial asthma and chronic obstructive pulmonary disease (COPD), whether subject is taking thiazide diuretics, oral contraceptives, or high-dose hormones or the like.

(3) The subjects can be classified, for example into 11 categories for use of different types of correlative formulas and different methods of blood glucose correction, according to their recent glucose levels, basal body temperature and basal metabolic rate, as well as physiological or pathological conditions.

(4) The instrument is initialized with the general body temperature-time curve, and then constantly modifies the original temperature-time curve from the measured basal body temperature and blood glucose with a large number of temperature test data, so that the instrument adjusts gradually its parameters to fit a specific subject's body temperature changes, which are used as the important parameters for its adaption in blood glucose measurement. In other words, initial GOx measurements, and periodic GOx measurements over the course of use of the instrument can be used to fit the empirical data to the specific individual.

5. Measurement and Calculation of Basal Body Temperature and basal Metabolic Rate The purpose to determine basal body temperature and basal metabolic rate is to identify the subject's current physical condition related to the metabolism. Through the classification and the selection of an appropriate self-correction formula, a variety of physiological and pathological aspects of interference can be corrected. Basal metabolic rate of the body is the heat dissipation in one hour from one square meter of body surface area under awake but extremely calm state. In this extremely calm condition, the subject's muscle activity and dynamic effects of mental stress, food, and environmental temperature and other factors can be ruled out.

(2) In general, basal body temperature and basal metabolic rate decreases with age, and is higher in men than in women. But as long as the testing conditions remain unchanged, the basal body temperature and the basal metabolic rate are generally very stable from the same subject at different times. Basal body temperature of women in reproductive age shows a change with menstrual period.

(3) The test conditions for the basal body temperature and the basal metabolic rate are: before eating in the morning (vegetarian food is recommended and taken 12-14 hours before test), lying with eyes closed for a half hour or more, excluding mental stress factors, and room temperature between 18-25° C. (64.4-77° F.).

(4) An infrared thermometer with ear probe measures the tympanic membrane temperature as a basal body temperature in one ear canal. The basal body temperature (by tympanic membrane measurement) for general population can be found in literature. The normal range is from 36 to 37.4° C. Average basal body temperature of women is about 0.3° C. higher than that of men. Beyond this range, 36 to 37.4° C. for men and 36.3 to 37.7° C. for women, pathological changes may occur. The instrument can be programmed to automatically save the measured basal body temperature.

(5) At the same time, in another ear canal for example, a blood glucose probe (for blood glucose index) measures the temperature rising value, $\Delta t$ in a fixed time period (e.g. 1 minute) or the $\Delta T$ (time) needed to achieve a preset $\Delta t$. The properties of the probe are determined by its material, structure, quality, shape and size, and its thermal parameters and initial temperature $t_0$. The basal metabolic rate can calculated for example as follows:

$$Q=60\lambda c\Delta t/(\mu L+\nu P-\kappa)$$

Where $\lambda$: scale factor, c: probe specific heat, $\Delta t$: temperature increase (° C.) within 1 minute after the probe is placed in ear, L: subject's height (m), P: subject's body weight (kg), $\mu$: the ratio coefficient (0.0061 for the Chinese), $\nu$: scale factor (0.0128 for the Chinese), and $\kappa$: constant (0.1529 for the Chinese).

(6) Metabolism Measurement

By comparing the measured basal metabolic rate of a subject with that of normal population, the metabolism of the subject can be determined. The basal metabolic rate of normal population can be found in literature. For example, the average rates of Chinese with age and gender are listed below:

| Age | 11-15 | 16-17 | 18-19 | 20-30 | 31-40 | 41-50 | 51 and above |
|---|---|---|---|---|---|---|---|
| Men | 46.7 | 46.2 | 39.7 | 37.7 | 37.9 | 35.8 | 35.6 |
| Women | 41.2 | 43.4 | 36.8 | 35.0 | 35.1 | 34.0 | 33.1 |

The percentage of the subject's basal metabolic rate over the average of normal population is calculated as below:

$$F=[(Q-B)/B]100\%$$

Where Q: subject's basal metabolic rate, B: the normal basal metabolic rate based on the race, gender and age of the subject.

The normal range is $-15\% \leq F \leq 15\%$. If F is +/−20% above normal, the pathological changes may occur. For example, inadequate thyroid function results in F 20-40% lower than its normal value; hyperthyroidism 25-80% higher. Patients with diabetes, polycythemia, leukemia and heart disease associated with breathing difficulties have increases in basal metabolic rate. In the nephrotic syndrome, Addison's disease, adrenal cortex and pituitary function and pathological hunger reduction result in F lower than the normal range. For subject with fever, the basal metabolic rate will rise. In general, every 1° C. increase in body temperature will result in the basal metabolic rate increase by 15%.

6. Principle of Subject's Classification

According to the subject's glucose level, basal body temperature and basal metabolic rate, as well as physiological or pathological conditions, the subject can be divided into categories, such as 11 categories:

Category 1: Normal population:
Fasting blood glucose (venous plasma): 3.9-6.1 mmol/L
2-hour postprandial blood glucose (venous plasma): 7.8-11.1 mmol/L
Basal body temperature (tympanic membrane): 36-37° C.
Basal metabolic rate range: $-10\% \leq F \leq 10\%$
Not suffering following diseases: hyperthyroidism, liver dysfunction, hypercortisolism, acromegaly, pancreatic disease, glucagon tumor, long-term low fever, polycythemia, leukemia and heart disease with respiratory difficulties, chronic bronchitis, bronchial asthma, emphysema and chronic obstructive pulmonary disease (COPD), severe hepatitis, cirrhosis or liver cancer and other serious liver disease and pancreatic β cell hyperplasia or insulinoma, kidney disease, Addison's disease, adrenal cortex and pituitary function associated with pathological hunger reduction, and other like as pathologies.

Not recently taking thiazide diuretics, oral contraceptives or high-dose hormone.

Category 2: Metabolism higher than normal population

Fasting blood glucose (venous plasma): 3.9-6.1 mmol/L 2-hour postprandial blood glucose (venous plasma): 7.8-11.1 mmol/L Basal body temperature (tympanic membrane): 37.0-37.5° C.

Basal metabolic rate range: $10\% \leq F \leq 20\%$

Not suffering following diseases: hyperthyroidism, liver dysfunction, hypercortisolism, acromegaly, pancreatic disease, glucagon tumor, long-term low fever, polycythemia, leukemia and heart disease with respiratory difficulties, chronic bronchitis, bronchial asthma, emphysema and chronic obstructive pulmonary disease (COPD), severe hepatitis, cirrhosis or liver cancer and other serious liver disease and pancreatic β cell hyperplasia or insulinoma, kidney disease, Addison's disease, adrenal cortex and pituitary function associated with pathological hunger reduction, and other like as pathologies.

Not recently taking thiazide diuretics, oral contraceptives or high-dose hormone.

Category 3: Metabolism lower than normal population

Fasting blood glucose (venous plasma): 3.9-6.1 mmol/L 2-hour postprandial blood glucose (venous plasma): 7.8-11.1 mmol/L Basal body temperature (tympanic membrane): 35.5-36.0° C.

Basal metabolic rate range: $-20\% \leq F \leq -10\%$

Not suffering following diseases: hyperthyroidism, liver dysfunction, hypercortisolism, acromegaly, pancreatic disease, glucagon tumor, long-term low fever, polycythemia, leukemia and heart disease with respiratory difficulties, chronic bronchitis, bronchial asthma, emphysema and chronic obstructive pulmonary disease (COPD), severe hepatitis, cirrhosis or liver cancer and other serious liver disease and pancreatic β cell hyperplasia or insulinoma, kidney disease, Addison's disease, adrenal cortex and pituitary function associated with pathological hunger reduction, and other like as pathologies.

Not recently take thiazide diuretics, oral contraceptives or high-dose hormone.

Category 4: Simple reduced glucose tolerance group

Fasting blood glucose (venous plasma): 6.1-7.0 mmol/L 2-hour postprandial blood glucose (venous plasma): 7.8-11.1 mmol/L Not suffering following diseases: hyperthyroidism, liver dysfunction, hypercortisolism, acromegaly, pancreatic disease, glucagon tumor, long-term low fever, polycythemia, leukemia and heart disease with respiratory difficulties, chronic bronchitis, bronchial asthma, emphysema and chronic obstructive pulmonary disease (COPD), severe hepatitis, cirrhosis or liver cancer and other serious liver disease and pancreatic β cell hyperplasia or insulinoma, kidney disease, Addison's disease, adrenal cortex and pituitary function associated with pathological hunger reduction, and other like as pathologies.

Not recently taking thiazide diuretics, oral contraceptives or high-dose hormone.

Category 5: Simple diabetics

Fasting blood glucose (venous plasma)≥7.0 mmol/L 2-hour postprandial blood glucose (venous plasma)≥11.1 mmol/L Basal body temperature (tympanic membrane): 36.5-37.5° C.

Basal metabolic rate range: $15\% \leq F \leq 40\%$

Not suffering following diseases: hyperthyroidism, liver dysfunction, hypercortisolism, acromegaly, pancreatic disease, glucagon tumor, long-term low fever, polycythemia, leukemia and heart disease with respiratory difficulties, chronic bronchitis, bronchial asthma, emphysema and chronic obstructive pulmonary disease (COPD), severe hepatitis, cirrhosis or liver cancer and other serious liver disease and pancreatic β cell hyperplasia or insulinoma, kidney disease, Addison's disease, adrenal cortex and pituitary function associated with pathological hunger reduction, and other like as pathologies.

Not recently taking thiazide diuretics, oral contraceptives or high-dose hormone.

Category 6: Simple increased metabolism

Fasting blood glucose (venous plasma): 3.9-6.1 mmol/L 2-hour postprandial blood glucose (venous plasma): 7.8-11.1 mmol/L Basal body temperature (tympanic membrane): 37.0-37.5° C.

Basal metabolic rate range: $20\% < F$

Suffering from hyperthyroidism, long-term low fever, polycythemia, leukemia, or heart disease with respiratory difficulties. Without chronic bronchitis, emphysema and bronchial asthma, chronic obstructive pulmonary disease (COPD); no severe hepatitis, cirrhosis or liver cancer and other serious liver disease and pancreatic β cell hyperplasia or insulinoma; no kidney disease, Addison's disease, adrenal cortex and pituitary function associated with pathological hunger reduction, and like such as pathologies;

Not recently taking thiazide diuretics, oral contraceptives or high-dose hormone.

Category 7: Simple extremely lower metabolism

Fasting blood glucose (venous plasma): 3.9-6.1 mmol/L 2-hour postprandial blood glucose (venous plasma): 7.8-11.1 mmol/L Basal body temperature (tympanic membrane): 35.5-36.0° C.

Basal metabolic rate range: $F < -20\%$

Suffers from kidney failure, Addison's disease, adrenal cortex and pituitary function and associated with pathological reduction in hunger, or other diseases. But not hyperthyroidism, liver dysfunction, hypercortisolism, acromegaly, pancreatic disease, glucagon tumor, long-term low fever, polycythemia, leukemia and heart disease associated with breathing difficulties; without chronic bronchitis, emphysema and bronchial asthma, chronic obstructive pulmonary disease (COPD); no severe hepatitis, cirrhosis or liver cancer and other serious liver disease and pancreatic β cell hyperplasia or insulinoma;

Not recently taking thiazide diuretics, oral contraceptives or high-dose hormone.

Category 8: Extremely increased blood glucose for non-diabetic population
Fasting blood glucose (venous plasma): ≥7.0 mmol/L
2-hour postprandial blood glucose (venous plasma): ≥11.1 mmol/L
Basal body temperature (tympanic membrane): 35.5-37.5° C.
Basal metabolic rate range: −10%≤F≤20%
Suffering from liver dysfunction, hypercortisolism, acromegaly, pancreatic disease, or glucagon tumor. But not hyperthyroidism, long-term low fever, polycythemia, leukemia and heart disease associated with breathing difficulties, and no severe hepatitis, cirrhosis or liver cancer and other serious liver disease and pancreatic β cell hyperplasia or insulinoma; no chronic bronchitis, lung swelling and bronchial asthma, chronic obstructive pulmonary disease (COPD);
Not recently taking thiazide diuretics, oral contraceptives or high-dose hormone.
Category 9: Low blood glucose group
Fasting blood glucose (venous plasma): <3.9 mmol/L
2-hour postprandial blood glucose (venous plasma): <7.8 mmol/L
Basal body temperature (tympanic membrane): 35.5-36.0° C.
Basal metabolic rate range: F≤−10%
Suffering from severe hepatitis, cirrhosis or liver cancer or have serious liver or pancreatic β-cell proliferation, or long-term malnutrition insulinoma. But not hyperthyroidism, long-term low fever, polycythemia, leukemia and heart disease associated with breathing difficulties; without chronic bronchitis, emphysema and bronchial asthma, chronic obstructive pulmonary disease (COPD),
Not recently taking thiazide diuretics, oral contraceptives or high-dose hormone.
Category 10: Combined diabetes
Fasting blood glucose (venous plasma) ≥7.0 mmol/L
2-hour postprandial blood glucose (venous plasma)≥11.1 mmol/L
Basal body temperature (tympanic membrane): 36.5-37.5° C.
Basal metabolic rate range: 25%≤F
Suffering from hyperthyroidism, liver dysfunction, hypercortisolism, acromegaly, pancreatic disease, glucagon tumor, long-term low fever, polycythemia, leukemia, or heart disease associated with breathing difficulties; but not chronic bronchitis, bronchial asthma, emphysema and chronic obstructive pulmonary disease (COPD); no severe hepatitis, cirrhosis or liver cancer and other serious liver disease and β-cell hyperplasia or insulinoma; no kidney disease, Addison's disease, adrenal cortex and pituitary function associated with pathological hunger reduction, or like pathologies;
Not recently taking thiazide diuretics, oral contraceptives or high-dose hormone.
Category 11: Chronic obstructive pulmonary disease (COPD) population
Fasting blood glucose (venous plasma): 3.9-6.1 mmol/L
2-hour postprandial blood glucose (venous plasma): 7.8-11.1 mmol/L
Basal body temperature (tympanic membrane): 35.5-37.5° C.
Basal metabolic rate range: −20%≤F≤20%
Not suffering following decease: hyperthyroidism, liver dysfunction, hypercortisolism, acromegaly, pancreatic disease, glucagon tumor, long-term low fever, polycythemia, leukemia and heart disease associated with breathing difficulties; nephropathy, A Dickson's disease, adrenal cortex and pituitary function associated with pathological hunger reduction, or like pathologies;
Not recently taking thiazide diuretics, oral contraceptives or high-dose hormone.
Category 12: Special group
Recently taking large doses of thiazide diuretics, oral contraceptives or hormones (such as prednisone).
Suffering AIDS
Taking antiviral drug
Suffering psychiatric disease
Suffering dehydration, hypoxia, asphyxia, coma, severe trauma and severe reactions among pregnant In the above categories, except the last category, the blood glucose can be obtained with a formula normalized to the category. Within a certain tolerance, the same formula may be shared for some categories (such as 1, 3, 4 and 5). For certain groupings, such as Category 12, it may be difficult to relate the data described here to blood glucose.

The categorization can be in part based on whether a normal range of fasting blood glucose or one or more ranges of elevated fasting blood glucose pertains. Or, it can be in part based on whether a low range, normal range, or elevated range of 2-hour postprandial blood glucose pertains. Or, it can be in part based on whether a low range, a normal range, or one or more elevated ranges of basal body temperature pertains. Or, it can be in part based on whether one or more low ranges, a normal range, or one or more elevated ranges of basal metabolism pertains.

The categorizations may result in the selection of one of two or more, or 3 or more, or 4 or more, or 5 or more, or 6 or more, or 7 or more, or 8 or more, or 9 or more, or 10 or more, or 11 or more separate empirical formulas (dependent on the categorizing).

7. Correction of Temperature-Time Curve (1) A unified body temperature-time curve reflecting the daily rhythm of the body temperature in general population is entered into the instrument, for instance according to the precision of clock display (the smallest unit of time coordinate programmed into the instrument, such as minutes). From the temperature-time curve, the value of the body temperature in general population can be obtained at any point in a day.

(2) The user is measures his/her basal body temperature with the instrument. The measured basal body temperature is used to replace the original value in the body temperature-time curve at the corresponding time.

(3) The user takes a number of measurements of the body temperature at different times, such as every half hour in non-sleep time. The measured body temperatures are used to replace of the original values in the body temperature curve at the corresponding time.

(4) Using the modified body temperature values at the time points, the temperature-time curve adapted for individual subject is obtained with a general interpolation method (such as the Lagrange interpolation formula).

(5) In an ongoing manner thereafter, the temperature values obtained at individual measurements of blood glucose can be used to replace the corresponding values in the curve. With an interpolation method, the curve is further modified to reflect the body temperature variation of the individual subject.

8. Blood Glucose Calibration

The Principle of Blood Glucose Calibration

As any non-invasive blood glucose detection methods, in an embodiment of the present invention, the blood glucose-related parameters measured under the certain conditions can be compared with benchmarks, i.e., the blood glucose levels from using an invasive method under the same conditions. These invasive values can be used to refine the conversion of the noninvasive parameters to blood glucose. This conversion can be a simple factor or analytical formula, a more complicated empirical formula, a curve or a table stored in the database, or other similar mathematical relationship. This comparison process under defined conditions is glucose calibration.

(2) Conditions for Glucose Calibration

In an embodiment of this invention, the blood glucose calibration can to be taken under the basal metabolic state, which is different from the aforementioned U.S. and Japanese patents. In other words, the conditions for the glucose calibration are the specific conditions of the basal metabolic state. If such conditions cannot be fully meet, an alternative conditions for the calibration of the noninvasive parameters is using fasting blood glucose levels by an invasive method in early morning, and then a conversion of the such approximate parameters to the blood glucose level can be obtained. Blood glucose measured by an invasive method at times not matching the noninvasive measurements introduce greater error, and are generally not preferred for calibration purposes.

(3) The General Operation for Blood Glucose Calibration

According to an operation embodiment of this invention, the calibration is taken by measuring the glucose level from the blood glucose probe and the tympanic membrane temperature probe, while at the same time the blood glucose level obtained from a conventional invasive blood glucose monitor (such as using glucose oxidase method). If the calibration value of the blood glucose level (such as calibration in the early morning fasting state, where fasting blood glucose varies slightly) is known, it can be directly entered into the instrument. However, if the blood glucose level at this time is uncertain, it is highly recommended to take an invasive test and obtain the blood glucose level for calibration.

(4) Re-Calibration

Glucose calibration is not done for "once and for all". When environmental conditions or subject's physiological or pathological conditions change, re-calibration is needed to maintain the accuracy of detection. The criterion for whether or not to re-calibrate include:

Environmental temperature and humidity, especially the former, affect the accuracy of blood glucose test significantly. The relationship between environmental temperature and humidity with the measured blood glucose is highly nonlinear, which cannot be calibrated with a limited number of non-linear formula for a large environmental temperature range. As an alternative, the environmental temperature can be divided into a number of range, and in the different ranges different blood glucose calibrations and the different correction formulas can be used. Obviously, the more detailed the division and the more narrow the temperature range, the more accurate of the measurement can be realized, but also the more inconvenient the operation of the instrument is, trade-offs need to be considered.

The guideline is that under sufficient measurement accuracy the environmental temperature range should be divided as small as practical. For example, the environmental temperature can be divided into five intervals as below 5° C., 5-10° C., 10-20° C., 20-30° C. and over 30° C. As the operation temperature of the instrument can conveniently be from 5-30° C., the division of the environmental temperature range can be the three intervals in middle. In the each interval, the calibration parameters should be adjusted for the environmental temperature, therefore the re-calibration is needed when the environmental temperature changes from one range to another range. Or, previous calibrations in these ranges can be called up for use in the instrument.

The measurement accuracy of blood glucose probe is also affected by the subject's physical, psychological or pathological conditions. If such conditions are temporary (such as cold), the instrument, it may be appropriate to use other methods of blood glucose measurement. If such conditions will exist for a long term (such as pregnancy, chronic illness, mental stimulation that needs time to recover), re-calibration should be taken under these conditions.

The measurement accuracy of blood glucose is also affected by the changes of the subject's habits, behaviors or life style. If such changes are temporary (such as participation in sports competitions, performances, examinations, over-eating and over-drinking), it may be appropriate to use other methods of blood glucose measurement. If such changes are for a long term (such as smoking cessation therapy, alcohol or drug dependence treatment, or taking a new job, etc.), re-calibration should be taken under these changes.

The measurement accuracy of blood glucose is also directly affected by the subject's diabetic condition or treatment changes. For example, if because of inadequate treatment blood glucose level is significantly increased, re-calibration should be taken under this glucose level. If under the guidance of doctor the subject's treatment is changed as to hypoglycemic drugs, insulin dosages or the like, re-calibration should be undertaken.

9. Methods for Blood Glucose Measurement and Calculation Major Procedures

Personal information is entered into an instrument through Q&A, by keyboard or touch-screen or the like. Useful information includes age, gender, weight, height, recent fasting blood glucose levels, recent 2-hour postprandial blood glucose levels (e.g., GOx), whether there is a long-term fever, hyperthyroidism, liver dysfunction, hypercortisolism, acromegaly, pancreatic disease, glucagon tumor, polycythemia, leukemia and heart disease associated with breathing difficulties, severe hepatitis, liver cirrhosis, liver cancer, pancreatic β cell proliferation, insulin tumor kidney disease, Addison's disease, adrenal cortex, pituitary function reduced pathological hunger or other diseases, whether subject to long-term malnutrition, whether taking thiazide diuretics, contraceptives, or large doses of hormones, whether pregnant, whether there is a serious reaction in pregnancy, or the like. Subjects should consult their doctors if they are uncertain about answers to the questions.

According to operation procedures, the basal body temperature and the basal metabolic rate are measured under the conditions described above.

According to operation procedures, a calibration is performed. The calibration can be done with the measurements of the basal metabolic rate and the basal body temperature, or separately, under the conditions described above. The instrument can be programmed to provide guidance to the user, such as via a display or voice synthesizer.

According to operation procedures, the following measurements are taken: the blood glucose noninvasive measurement, and at the same time the tympanic membrane temperature, environmental temperature and relative humidity, local relative humidity in ear canal, blood oxygen concentration, and pulse.

(2) Methods for Metabolic Heat Collection

There are for example two methods for the data collection:

Place the blood glucose noninvasive probe (having a fixed physical parameters (mass, material, structure, size and specific heat, etc.) an embedded temperature sensor, and a certain initial temperature $t_0$) into the ear canal. The initial temperature, the temperature increase, and the duration $\Delta T$ of the temperature increase from $t_1$ to $t_2$ are recorded. Here, the temperature differences, $(t_1-t_0)$ and $(t_2-t_1)$ are fixed values, and the operative parameter is duration. Much of the exemplification below operates on this method Place the blood glucose probe (being a fixed physical parameters (mass, material, structure, size and specific heat, etc.) an embedded temperature sensor, and a certain initial temperature $t_0$) into the ear canal. The temperature increase $\Delta t$ over a preset time period is recorded. The "glucose probe" of "blood glucose probe" functions according to a method such as outlined above that is dependent on temperature and heat flux.

(3) Principles to Determine the Initial Temperature of the Probe

Regardless the external environment conditions, the initial temperature of the probe should generally be not higher than 35° C.

The initial temperature of the probe depends on the environmental temperature and humidity. The higher the environmental temperature and humidity, the higher initial temperature is, and vice versa.

The default initial temperature can be set by the empirical formula $t_0=f(t_h, p_h)$, in which $t_h$ and $p_h$ represent the environmental temperature and humidity, or by a table in the instrument presetting the initial temperature with the environmental temperature and humidity.

Accuracy for temperature measurement should preferably be higher than +/−0.1° C., and resolution 0.05° C. or better.

(4) Realization of the Initial Temperature of Blood Glucose Probe

Through the heating or cooling components in the instrument, the desired initial temperature can be directly set.

The probe can be heated to a temperature above its initial temperature, and then cooled in air to the desired initial temperature. Heating can be done by heating elements contacted with the probe. The subject's body temperature can be also used to heat the probe to above its initial temperature by placing the probe under armpit or in oral cavity.

The advantage of the latter approach is easy to control the accuracy of the desired initial temperature and it eliminates the need of the cooling components.

(5) Calculation of Blood Glucose

In the present invention, the user current blood glucose is a function of a series of parameters.

For the subjects in the above Category 1, the function can be:

$$Q=f_1(\Delta T, \Delta T_w, t_h, t_b, p_h, p_b, p_w, p_{wb}, t_w, t_{wb}, y_w, y_{wb}, m_w, m_{wb})$$

For the subjects in the above Category 2, the function is:

$$Q=f_2(\Delta T, \Delta T_w, t_h, t_b, p_h, pb, p_w, p_{wb}, t_w, t_{wb}, y_w, y_{wb}, m_w, m_{wb})...$$

And so on. For the subjects in the different category, the function is different. However, the same function can be used for the subjects in Category 1, 3, 4 and 5, within the accuracy, in which:

$\Delta T$ is in the current measurement the duration of the probe temperature increase from $t_1$ to $t_2$, when the probe with its fixed physical parameters is placed in ear canal and its initial temperature increases from the temperature $t_0$ that is set from the current environmental temperature $t_h$ and humidity $P_h$.

$\Delta Tw$ is in the most recent blood glucose calibration, the duration of the probe temperature increase from a $t_{b1}$ to $t_{b2}$, when the probe with its fixed physical parameters is placed in ear canal and its temperature increases from the initial temperature $t_{b0}$ that is set from the current environmental temperature $t_b$ and humidity Pb. Note: $(t_1-t_2)=(t_{b1}-t_{b2})$ $t_h$ is the current environmental temperature.

$t_b$ is the environmental temperature when the most recent or otherwise most relevant calibration is taken.

$P_h$ is the current relative environmental humidity.

$p_b$ is the environmental relative humidity when the most recent or otherwise most relevant calibration is taken.

$p_w$ is the current relative humidity inside ear.

$p_{wb}$ is the relative humidity inside the ear when the most recent or otherwise most relevant calibration is taken.

$t_w$ is the current tympanic membrane temperature.

$t_{wb}$ is the tympanic membrane temperature when the most recent or otherwise most relevant calibration is taken.

$y_w$ is the current blood oxygen.

$y_{wb}$ is the blood sugar oxygen saturation when the most recent or otherwise most relevant calibration is taken.

$m_w$ is the current pulse in one minute.

$m_{wb}$ is the pulse when the most recent or otherwise most relevant calibration is taken.

A more specific function for category 1 can be written:

$$V=\lambda\{k_0 C\alpha + k_1 T_b(T-T_b)\beta + k2[(J-H)-(J_b-H_b)]^\gamma + k_3[(t-tc)-(tb-tbc)]^\delta + k(y-yb)^\epsilon + k5(m-mb)^\zeta\} \quad (3)$$

where V is the blood glucose value, $\lambda$ is the calibration coefficient, $C=100/(P_2-P_1)$, where $P_2$ and $P_1$ are, respectively, the corresponding time points when the probe temperature is at $d_1$ and time when it reaches temperature $d_2$ ($d_2>d_1$). $d_1$ can be determined dependent on current ambient temperature T and ambient humidity H. $d_2$ can be a preset value.

$T_b$ is the ambient temperature measured at last calibration,

J is current local ear cavity humidity, $J_b$ and $H_b$ are the local ear cavity humidity and ambient humidity obtained at last calibration, t is the current tympanic temperature, $t_c$ is the tympanic temperature at corresponding time from the body temperature-time curve which is stored in the meter, while $t_b$ and $t_{bc}$ are the tympanic temperatures at corresponding calibration time from the tympanic temperature-time curve and the body temperature-time curve which were calibrated most recently.

y is the current saturated concentration of blood oxygen, $y_b$ is the saturated concentration of blood oxygen at last blood glucose calibration.

m is the current pulse number per minute, $m_b$ is the pulse number per minute at last blood glucose calibration.

$\alpha, \beta, \gamma, \delta, \epsilon, \zeta, k_0, k_1, k_2, k_3$, and $k_4$ are empirical parameters that must be determined by experiments.

For the subjects of other Categories, the calculation formula for their blood glucose can have a same form as above formula (3), but the parameters $\alpha, \beta, \gamma, \delta, \epsilon, \zeta, k_0, k_1, k_2, k_3$, and $k_4$ can be different.

(6) Detection of Environment temperature and its Effects on Blood Glucose Measurement Thermistor, temperature sensitive diode, thermocouple, thermal resistance, temperature sensor IC, or other conventional components can be used as temperature sensor.

The sensor accuracy should be greater than +/−0.1° C. with its resolution more than 0.05° C.

The sensor should preferably be installed a certain distance away from the subject to avoid the radiation heat from the body.

As environmental temperature increases, the body heat will inevitably increase, while blood glucose is not elevated with the environmental temperature, the glucose level from the measurement of the radiation heat will be higher than its actual value. Therefore, if the environmental temperature is higher than the temperature at the calibration, the glucose level should be corrected to a lower level. The present invention realized such correction according to the probe initial temperature determined from the environmental temperature and humidity. Meanwhile, the correction is further performed in the calculation function according to the difference between the current environment temperature and the temperature at the calibration.

The measurement of the blood glucose is affected seriously under the environmental temperature close to 0° C. or above 35° C., when the body suffers chilling or sweating, which is very difficult to correct such errors. Therefore, the operation temperatures can be clearly defined, such as from 5° C. to 30° C. Beyond that, the instrument can be programmed to display a failure signal.

(7) Detection of Environment Relative Humidity and its Effects on Blood Glucose Measurement Lithium chloride film, coated carbon film, selenium evaporation film, sintered ceramic, humidity sensor, or other conventional components can be used to provide a humidity sensor.

The sensor accuracy should preferably be greater than +/−2%, with its resolution more than 1%.

The sensor should be installed a certain distance away from the subject to avoid the sweating moisture from the body.

As environmental humidity increases, the body temperature, including the temperature in ear canal will inevitably increase due to heat dissipation in evaporation is blocked, which will result in the glucose level from the measurement higher than its actual value. Therefore, the glucose level should be corrected by the environmental humidity. The present invention realized such correction according to the probe initial temperature determined from the environmental temperature and humidity. In addition, the correction is further performed in the calculation function according to the difference between the current environment humidity and the humidity at the calibration. In general, the accuracy of blood glucose measurement is affected less from the environmental humidity than the temperature.

The measurement of the blood glucose is affected severely under the environmental relative humidity close to 0% or 100%, when the heat dissipation in evaporation goes through a rapid change. It is very difficult to correct such errors. Therefore, the operation range of humidity can be clearly defined, such as from 5% to 95%. Beyond that, the instrument can be programmed to display a failure signal.

(8) Detection of Local Relative Humidity in Ear Canal and its Effects on Blood Glucose Measurement The requirements of the detection for the local relative humidity in ear canal are basically same as that for the environmental relative humidity, except that the sensor size should be small enough to be placed in the vicinity of the tympanic membrane. The correction is performed in the calculation function according to the difference between the current local humidity and the humidity at the calibration. When the ears relative humidity exceeds a certain value (such as 95%), sweating in ear is very serious, rendering it difficult to correct the glucose measurement. At such circumstance, the instrument can be programmed to display a failure signal.

(9) Detection of Body Temperature (Tympanic Temperature) and its Affects on Blood Glucose As the infrared wavelength (9-10 μm) emission from the body temperature at 36-37° C. falls in far-infrared range, far-infrared detection components such as pyroelectric infrared sensors can be used in an assembly in a tympanic temperature probe. A near-infrared device (such as infrared photosensitive diode or transistor) are disfavored.

The sensor accuracy should preferably be greater than +/−0.1° C. with its resolution more than 0.05° C.

The size and shape of the sensor should allow it to be placed into a deep position in ear canal. For simultaneous detection with the blood glucose and avoiding interference with the glucose probe, the glucose probe and the temperature and humidity probe for the tympanic temperature and the local moisture can be concurrently placed into alternate ear canals (such as the left and the right ear canal respectively).

Experiments showed that at each 1° C. increase in body temperature, the basal metabolic rate will be increased by 13%. However, blood glucose and body temperature are not necessarily related, the blood glucose level measured from the body heat dissipation is higher than the actual value. In the present invention, the blood glucose level is corrected with the tympanic temperature difference between the current measurement and the calibration value. For example, if without the correction, the blood glucose level may be measured more than 15% higher at 4-5 PM than in the early morning, because the body temperature reaches its peak at 4-5 PM, that is 0.5° C. higher than the early morning. Another example, women in their childbearing age have their body temperature changes before and after ovulation, which will affect the accuracy of blood glucose measurement.

With the increase in the number of the usage, an instrument operating the method can constantly modify the original temperature-time curve, and gradually adapt the curve function in the instrument to the users body temperature pattern. The measurements of the tympanic temperatures can then be compared with the body temperature-time curve, and if an abnormal situation is found, the instrument can be calibrated to remove interferences. For example, in a blood glucose measurement, if the tympanic membrane temperature measured at the certain time is significantly higher than the value in the normal body temperature-time curve, but the environmental temperature and humidity are normal, the blood oxygen concentration does not change much, but the pulse may be slightly faster. The instrument can analyze such situation and consider that the subject may just have intense exercise, a hot bath, or is suffering a fever. Another example, if the tympanic temperature is slightly higher after a meal, and other parameters are normal, the instrument will consider the temperature increase may due to dynamic effects of specific foods. If the temperature is increased too much with the fast pulse, the food intake may be a reason, such as taking high concentrations of alcohol or spicy food. The instrument can automatically exclude such errors by accounting for the difference between the measurement and the value in the curve.

The measurement of the blood glucose is severely affected when the body is in abnormal state such that the tympanic temperature is departing too much (higher or lower) from the normal body temperature-time curve. Such departure makes it difficult for the instrument to correct the errors. Therefore, the tympanic temperature range is clearly defined. Beyond that range (such as 1° C. or 2° C. or 3° C. lower or higher than the normal temperature for the individual), the instrument can be programmed to display a failure signal.

(10) Detection of Blood Oxygen and its Effects on Blood Glucose Level

Using noninvasive oxygen saturation (dissolved oxygen) sensor probe (commercially available).

The sensor accuracy should preferably be higher than +/−2%, resolution, better than 1%, and its detection range, 30-99%.

The sensing position is for example on a finger, so that the finger should be cleaned of sweat and dirt.

Because actual blood glucose does not decrease with the decrease of the blood oxygen, measured blood glucose can be below the actual value when the heat production is decreased due to decreases in blood oxygen and associated decreases in metabolic rate. Therefore, the measured blood glucose should be corrected according to the oxygen concentration difference between the current value and at calibration. Except for the patients suffering trachea, lung or heart disease from respiratory dysfunction, the blood oxygen varies very little in general population. In chronic obstructive pulmonary disease (COPD) such as chronic bronchitis, emphysema and bronchial asthma, airway obstruction may occur, which will result in the decrease of the blood oxygen. For acute or severe COPD, oxygen saturation is reduced to less than 90%; moderate acute asthma, the oxygen in the 91-95% range; and mild COPD, oxygen typically greater than 95%. After breathing oxygen, the patient's oxygen level will be significantly increased in a short period. Comparing with temperature and other factors, blood oxygen shows a smaller effect on the accuracy of blood glucose measurement.

The measurement of the blood glucose is affected seriously when the subject suffers severe COPD or excessive oxygen, that is the oxygen saturation is lower than 90% or higher to 100%, and it is difficult to correct such errors. Therefore, the appropriate range of the blood oxygen can be clearly defined. Beyond that (such as below 90% or higher than 99%), the instrument can be programmed to display a failure signal.

(11) Detection of Pulse and its Effects on Blood Glucose Measurement

Using noninvasive piezoelectric ceramic or infrared pulse sensor (commercially available).

Sensor accuracy should preferably be better than +/−1/min, and detection range of 40-350/minute.

The sensing position can be, for example, on a finger, so that the finger should be cleaned of sweat and dirt.

Because actual blood glucose is not related with the pulse, measured blood glucose can be higher than the actual values when the heat production is increased due to the increase of the pulse blood flow. Therefore, in embodiments of the present invention, the measured blood glucose level can be corrected according to the pulse difference between the current value and that at calibration.

The measurement of the blood glucose is affected seriously when the subject's pulse is significantly higher (for example, more than 100%) than that at calibration, in which the subject may suffer from a severe physical or psychological condition (such as intense exercise, fever, seriously stimulation, mental stress, fear, etc.). Therefore, the appropriate range of the pulse number can be clearly defined. Beyond that (such as the current pulse is 100% higher than that at calibration, or at any time, the pulse is greater than a certain value, such as 150), the instrument can be programmed to display a failure signal.

10. Instruments Parts

Detection Probe for Blood Glucose

The probe for glucose includes for example of a temperature sensor and an external protective material. As a solid body, the probe can have its specific material, its specific structure, its specific mass, its specific shape, size and dimension, and its specific thermal parameters. The term specific material refers to metal, ceramic, plastic or other appropriate materials. The term specific structure refers to the temperature sensor placed in the outer protective material (e.g., center), for example in a cylindrical or columnar shape. The specific thermal parameters refers to the overall heat capacity of the probe, specific heat, thermal conductivity and other parameters. With the determined material, structure, quality, shape and size, these parameters are basically fixed for a given probe. The phrase, "initial temperature" of the blood glucose monitoring probe is overall temperature of the probe before the measurement.

The temperature sensor is a device or a component that senses temperature changes through contact heat conduction, convection and/or radiation, which can include a thermocouple, thermistor, semiconductor PN junction, quartz crystal temperature sensor, pyroelectric infrared sensor, or other non-contact temperature sensors including non-contact temperature sensors. Useful properties include (1) accuracy greater than 0.1° C., (2) response time less than 5 seconds, (3) the probe gives little interference to detection temperature field (that is, the heat capacity of the probe should be as small as practical), (4) high reliability, and (5) small size.

Because contact heat conduction is affected by the tightness between the probe and the skin, the measurement of the blood glucose is seriously impacted if the tightness is different between the current measurement and at the calibration. Convection and radiation heat exchange are non-contact measurements, so that even if the location of the probe into the ear is slightly different, the measurement is—little affected. Therefore, in an embodiment of this invention, the blood glucose probe is covered with an outer protective material which provides good thermal insulation. Metal parts in the probe preferably do not directly contact with the skin, so that the contact heat conduction is reduced.

The probe can be made with its shape and size to be fitted in the ear, such that a local chamber can be formed, which sealed or enclosed sufficiently to thereby provide improved reproducibility.

(2) Other Probe

The probe for of environmental temperature can be a conventional temperature detection technology with inhouse-made or purchased sensor assembly. The probe is placed in the instrument or otherwise away from the subject.

The probe for environmental humidity can be a conventional technology with an assembled or purchased sensor assembly. The probe is placed in the instrument or otherwise away from the subject.

The sensor for tympanic temperature or other surrogate of core temperature can for example include conventional infrared temperature sensing technology, or another appropriately responsive and accurate temperature sensing technology. The sensor for local humidity can for example comprise conventional humidity sensor technology. Both sensors can be assembled within a common probe assembly. The size and shape of the probe can be such that it is able to fit into the ear canal or another body cavity.

The probe for blood oxygen ican be a conventional noninvasive blood oxygen saturation detection technology with an assembly from a purchased sensor. The probe is placed in the instrument or in communication with the instrument.

The probe for pulse detection is adopted a conventional pulse sensor technology with an assembly from a purchased sensor. The probe is placed in the instrument or in communication with the instrument.

(3) Probe Positioning

To ensure greater accuracy, the position and the depth of the blood glucose probe in the ear canal at the each measurement and during calibration should be as close to standardized as possible. Therefore, for example the following procedures can be used:

Probe A assembled with a blood glucose sensor and external insulation protective layer, and Probe B assembled with a tympanic temperature sensor and a local humidity sensor. The probes are placed and positioned separate ears. The size, shape and elasticity of the probe assemblies can help ensure reproducible placement of the probes, for example close to the tympanic membrane.

The shape of the two probes can be designed to conform to the internal shape of human ears, so the probes fit in the ear with sufficiently tightness, which reduces interference of external environmental factors and also ensures the probes to be positioned in ears consistently at the each measurement.

Different sizes of the probes can be designed to fit the different diameters of ear canals or the like.

The probes can also be personalized in its shape and size for use with a specific individual.

(4) Heating/Cooling Component in the Blood Glucose Probe

Presenting initial temperature of blood glucose probe from current environmental temperature and humidity can be realized with the following methods:

Using a conventional heating/cooling technology. For example, a semiconductor device is used in the instrument to heat or cool the probe to a desired initial temperature by contacting the probe with the device. For example, KIT66 127P-N junction cell from KIT-SRUS (US) works at 13V as a heater with a positive voltage and a cooler with a negative. A temperature sensor and feedback loop can be used to achieve a set-point temperature.

As mentioned above, to improve the accuracy of the initial temperature on the probe, the instrument can be designed with a heater only. The temperature on the heater is slightly over the preset initial temperature. By contacting the probe with the heater first and then removing from it, the initial temperature on the probe can be reached through air cooling.

Heating the blood glucose probe to the body temperature. For example, the probe is first placed under armpit for a minute or so for its temperature over the initial temperature, cooled in air to the desired initial temperature, and then placed in ear (or other cavity) for measurement.

(5) Alarm Components with Sound and Light

The instrument can in some embodiments give a sound/light indication or alarm signal when the probe reaches the desired initial temperature, when invalid measurement occurs, or when the level of glucose is far above or below the normal blood glucose values. A buzzer or a LED component can be used can be incorporated into the instrument or microprocessor used to manage the method. These components can be purchased and assembled or manufactured through a professional provider.

The invention described with particular reference to the preferred measurement site of the ears, and the preferred use of separate glucose probes and local temp./humidity probes. Other body cavities can be used with appropriate calibration, as can consolidated single probes having a number of the above functions, for example for use in a single cavity. Exemplary body cavities include the ear canal, mouth, armpit (held closed to form a cavity for an appropriate amount of time), urethra, anal canal, surgically artificial cavities, and the like. Where two or more cavities are used (for separate measurements) either comparable cavities are used, or the relationship between the two is normalized by calibration.

The method (measuring the input data indicated for formula (3) and appropriate correlative formulas) has been tested in a recent clinical trial with 45 subjects conducted in China. Six different correlative formulas were used depending on patient categorization. Compared with test results obtained from an automatic biochemical analyzer, the correlation coefficient of the data from deduced with the method of the invention is 0.975.

The method of the invention can be conducted with an automated glucose index ("AGI") detector 100. As illustrated in the FIGURE, a controller 50 can be attached to (which in all cases can mean attachable to) one or more of a probe 10 for the blood glucose index, a probe 12 for local humidity and/or temperature (which function or functions can be incorporated into probe 10) (the local/body temperature probe can be for tympanic temperature), an environmental temperature detector 14, and environmental humidity detector 16, a heart rate detector 18, a blood oxygen detector 20, and detectors for any other noninvasive measure of body function. The controller 50 can connect to an input device 60, which can be used for example to input medical history data that can be used to categorize the patient. The input device can, for example, provide a questionnaire that, in conjunction with data obtained by or stored in the AGI detector (such as prior measurements, basal metabolism measurements, and the like), be used to identify an appropriate category and correlation function for the patient. In one embodiment, the AGI detector is programmed to seek, via the input device and data inputs, all the information needed to categorize the patent. In one embodiment, the AGI detector prompts the patient or the caregiver for the physiological inputs needed, and identifies the conditions needed for measurement of such physiological inputs (e.g., basal conditions). The controller can be operated to operate, with prompts and instructions to the user or caregiver as needed, the methods described above.

The controller 50 comprises a central processing unit (CPU) 54, a memory 52, and support circuits 56 for the CPU 54 and is coupled to and controls one or more of the various elements of the AGI device 100 or, alternatively, via computers (or controllers) associated with AGI device 100. The controller 50 may be one of any form of general-purpose computer processor that can be used for controlling various devices and sub-processors. The memory, or computer-readable medium, 52 of the CPU 54 may be one or more of readily available memory such as random access memory (RAM), read only memory (ROM), flash memory, floppy disk, hard disk, or any other form of digital storage, local or remote. The support circuits 56 are coupled to the CPU 54 for supporting the processor in a conventional manner. These circuits can include cache, power supplies, clock circuits, input/output circuitry and subsystems, and the like. Methods of operating the AGI device 100 may be stored in the memory 52 as software routine that may be executed or invoked to control the operation of the AGI device 100. The software routine may also be stored and/or executed by a second CPU (not shown) that is remotely located from the hardware being controlled by the CPU 54.

This invention described herein of a method for noninvasive blood glucose monitoring. Although some embodiments have been discussed above, other implementations and applications are also within the scope of the following claims. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

What is claimed is:

1. A method for noninvasively determining blood glucose in a subject, comprising:
   setting an initial temperature for a blood glucose index probe, wherein the blood glucose index is a period for a defined temperature rise or temperature rise for a defined period;
   in body cavity(s) measuring:
      the blood glucose index with the initialized blood glucose index probe; and
      a local humidity;
   measuring an environmental temperature;
   measuring an environmental humidity; and
   deducing from the measured values and calibration data including chemically measured blood glucose the current blood glucose value.

2. The method of claim 1, further comprising measuring a basal body temperature, wherein the deducing is from the measured values including the basal body temperature.

3. The method of claim 1, further comprising measuring a basal metabolism, wherein the deducing is from the measured values including the basal metabolism.

4. The method of claim 1, further comprising measuring a body temperature, wherein the deducing is from the measured values including the body temperature.

5. The method of claim 4, wherein the blood glucose index is measured in one ear canal, and the local humidity and body temperature are measured in the second ear canal.

6. The method of claim 1, wherein the a blood glucose index is measured in an ear canal.

7. The method of claim 6, wherein the local humidity and body temperature are measured in an ear canal.

8. The method of claim 1, further comprising measuring one or more of a pulse or a blood oxygen level, wherein the deducing is from the measured values including the pulse and/or blood oxygen level.

9. The method of claim 1, further comprising:
   inputting data including one or more of fasting blood glucose, 2-hour postprandial blood glucose, basal body temperature, basal metabolic rate or medical condition data;
   categorizing the subject into one of at least two categories;
   selecting one of two or more separate empirical formulas dependent on the categorizing; and conducting the deducing with the selected empirical formula.

10. The method of claim 9, wherein the categorization is in part based on whether a normal range of fasting blood glucose or one or more ranges of elevated fasting blood glucose pertains.

11. The method of claim 9, wherein the categorization is in part based on whether a low range, normal range, or elevated range of 2-hour postprandial blood glucose pertains.

12. The method of claim 9, wherein the categorization is in part based on whether a low range, a normal range, or one or more elevated ranges of basal body temperature pertains.

13. The method of claim 9, wherein the categorization is in part based on whether one or more low ranges, a normal range, or one or more elevated ranges of basal metabolism pertains.

14. The method of claim 1, wherein calibration data including chemically measured blood glucose includes data taken under the basal metabolic state.

15. The method of claim 14, wherein calibration data including chemically measured blood glucose further includes data taken the subjects more current physiological state.

16. The method of claim 1, wherein the blood glucose index is measured in one ear canal, and the local humidity is measured in the second ear canal.

17. The method of claim 1, wherein deducing utilizes a estimate for the normal body temperature at the given time of day of the operation of the method, and wherein the estimate for various times of day are refined from data collected with each operation of the method.

18. An apparatus for measuring the blood glucose in a subject comprising:
   a controller;
   connected to the controller, a blood glucose index probe;
   connected to the controller, local humidity probe;
   connected to the controller, an environmental temperature probe; and
   connected to the controller, an environmental humidity probe;
   a heater and/or cooler for bringing the blood glucose index probe to an initial temperature,
   wherein the controller is programmed to deduce from values obtained from the probes and calibration data including chemically measured blood glucose the current blood glucose value, wherein the blood glucose index is a period for a defined temperature rise or temperature rise for a defined period.

19. The apparatus of claim 18, wherein the controller is connected to a probe local temperature and/or a probe for heart rate and/or a probe for blood oxygen saturation, and uses the values obtained from one or more of these probes to deduce the current blood glucose value.

20. The apparatus of claim 18, wherein the controller is connected to a probe local temperature, a probe for heart rate and a probe for blood oxygen saturation, and uses the values obtained from these probes to deduce the current blood glucose value.

21. The apparatus of claim 18, wherein the blood glucose index and the local humidity probes are configured to fit in separate ear canals.

\* \* \* \* \*